US006299891B1

(12) United States Patent
Leverett

(10) Patent No.: US 6,299,891 B1
(45) Date of Patent: Oct. 9, 2001

(54) OIL-FREE COSMETIC COMPOSITION

(75) Inventor: Jesse C. Leverett, Rockford, MI (US)

(73) Assignee: Amway Corporation, Ada, MI (US)

( * ) Notice: Subject to any disclaimer, the term of this patent is extended or adjusted under 35 U.S.C. 154(b) by 0 days.

(21) Appl. No.: 09/525,149

(22) Filed: Mar. 14, 2000

(51) Int. Cl.$^7$ .............................. A61K 7/00; A61K 7/021; A61K 7/42; A61K 31/74
(52) U.S. Cl. ..................... 424/401; 424/63; 424/78.03; 424/59
(58) Field of Search ................... 424/401, 78.02, 424/65, 63, 59

(56) References Cited

U.S. PATENT DOCUMENTS

| | | |
|---|---|---|
| 4,341,799 | 7/1982 | Good ................................. 424/365 |
| 4,829,092 | 5/1989 | Nelson et al. ........................ 514/738 |
| 4,863,725 | 9/1989 | Deckner et al. ........................ 424/81 |
| 5,489,429 | 2/1996 | Griat et al. ............................ 424/401 |
| 5,639,463 * | 6/1997 | Kilpatrick-Liverman ........... 424/401 |
| 5,723,137 | 3/1998 | Wahle et al. ......................... 424/401 |
| 5,849,278 | 12/1998 | Piot et al. ............................ 424/70.7 |
| 5,866,144 | 2/1999 | Chopra et al. ....................... 424/401 |
| 5,882,663 | 3/1999 | Koeniger et al. .................... 514/762 |
| 5,961,997 * | 10/1999 | Swinehart ............................. 424/401 |

* cited by examiner

Primary Examiner—Thurman K. Page
Assistant Examiner—Blessing Fubara
(74) Attorney, Agent, or Firm—Brinks Hofer Gilson & Lione

(57) ABSTRACT

An oil-free cosmetic composition comprising a plasticizer, a glycol, a metal soap, pigment, and water is provided. The cosmetic composition is preferably in the form of a stick.

21 Claims, No Drawings

OIL-FREE COSMETIC COMPOSITION

The present invention relates to an oil-free cosmetic composition in the form of a stick. The stick has surprisingly good pay-off properties; that is, it transfers pigment from the stick to skin very well.

Previously, many water-based oil-free cosmetic compositions have had poor spreadability. This problem was well-recognized in the art, so anhydrous oil-free cosmetics were used to address the spreadability problem. Although anhydrous oil-free cosmetic compositions had improved spreadability, they had other problems. One such problem was that anhydrous cosmetic compositions had poor pay-off properties. For this reason, anhydrous cosmetics, especially when formulated into a stick, were not particularly effective as make-up foundations.

An oil-free cosmetic stick is needed that addresses this problem.

SUMMARY

The present invention provides an oil-free cosmetic composition containing a plasticizer, a glycol, a metal soap, a pigment and water. This cosmetic composition is preferably in the form of a stick. Further, the cosmetic composition is preferably used as a make-up foundation to apply pigment to skin. The cosmetic composition is convenient for use in moisturizing make-up, foundation make-up, and blushes.

Preferably, the cosmetic composition also hydrates, moisturizes, and increases the firmness of skin. Preferably, the cosmetic composition has superior spreadability, good moisturizing ability, and feels pleasant on the skin. Preferably, this cosmetic composition has a strength such that is resistant to breakage or damage.

In one aspect, the invention provides an oil-free cosmetic composition comprising from about 0.5% to about 25% plasticizer, from about 1% to about 50% of glycol from about 2% to about 15% of a metal soap, from about 2% pigment to about 35% pigment, and from about 35% to about 70% of water. Unless otherwise stated, all percentages given in this specification and the appended claims refer to percentages by weight.

DETAILED DESCRIPTION OF THE PREFERRED EMBODIMENTS

The oil-free cosmetic composition of the present invention generally includes a plasticizer, a glycol, a metal soap, pigment, and water. The cosmetic composition is preferably in the form of a stick, and it can be used in moisturizers, foundation make-up, sunscreens, and skin-whiteners, and the like. The cosmetic composition can also be used in deodorants and antiperspirants and the like. Moreover, the cosmetic composition can be used to deliver medicaments, antioxidants, and the like.

PLASTICIZER

The plasticizer for use in the cosmetic composition of the present invention may be any of the water-soluble plasticizers listed in McCutcheon's Functional Materials, Vll, 1992. Preferably, the plasticizer is a water-soluble wax, or a non-water soluble wax that is modified so that it becomes water-solube. The water-soluble wax may be natural or synthetic. Generally, any water-soluble wax that effectively carries pigment (that is, the wax allows pigment to disperse consistently and has good pay-off) and serves as a plasticizing agent is a wax contemplated by this invention.

The most preferred plasticizers for use in the cosmetic composition of the present invention include polyethylene glycol 80, polyethylene glycol 120, dimethicone copolyol, ethoxylated jojoba wax, ethoxylated beeswax, and mixtures thereof. Jojoba wax PEG-80 esters and jojoba wax PEG-120 esters may be used. Methoxy derivatives of water-soluble PEGs may also be used.

Plasticizers contemplated for use in the cosmetic composition of the present invention include water-soluble organopolysiloxanes. Organopolysiloxanes may be rendered soluble either by chemical modification, or physically by the addition of a compound such as a surfactant. They may be used alone or mixed. In particular, as a chemically solubilized organopolysiloxane, a copolymer of siloxane and hydrolysed or unhydrolysed protein, as described in the document EP-A-540,357, the disclosure of which is hereby incorporated by reference, may be used. Examples of such copolymers are the copolymers of polysiloxane or derivatives linked covalently by grafting to a protein, hydrolysed or unhydrolysed, such as casein, elastin, collagen, keratin, silk or a wheat or soya protein.

Other organopolysiloxanes that may be used in the cosmetic composition of the present invention are dimethicone copolyols and their derivatives. Dimethicone copolyols are provided by DOW CORNING, and are reported in the publication "Water-soluble dimethicone copolyol waxes for personal care industry" by Linda Madore et al., pages 1 to 3.

The plasticizer is used in cosmetic composition of the present invention in an amount from about 0.5% by weight to about 25% by weight, preferably from about 5% to about 20%, and more preferably from about 7% to about 10%.

GLYCOL

Preferred glycols of the present invention include $C_{1-15}$ alkyl and $C_{1-15}$ alkenyl glycols. Preferred glycols are water-soluble. Particularly preferred glycols include propylene glycol, diethylene glycol, butylene glycol, and hexylene glycol. Generally, any glycol that effectively solubizes the metal soap and provides sufficient softening and moisturizing abilities to the cosmetic composition is a glycol contemplated by this invention.

The glycol is used in cosmetic composition in an amount from about 1% by weight to about 50% by weight, preferably from about 5% to about 40%, and more preferably from about 10% to about 30%.

METAL SOAPS

Preferred metal soaps of the present invention include sodium stearate, magnesium stearate, and mixtures thereof. Preferred metals soaps are water soluble, at least in the presence of a glycol. Generally, any metal soap that serves as a viscosity increasing agent and/or thickener is a metal soap within the scope of this invention. Generally, sodium soaps are used to formulate sticks, with stick hardness being proportional to the level of sodium stearate. Potassium soaps may be used to form softer matrices.

A non-limiting list of contemplated metal soaps follows: sodium palmitate, sodium stearate, magnesium stearate, potassium stearate, potassium palmitate, potassium myristate, and sodium myristate. Other contemplated metal soaps include those identified in U.S. Pat. No. 5,424,070, the contents of which are hereby incorporated herein by reference.

The metal soap used in cosmetic composition of the present invention in an amount from about 2% by weight to about 15% by weight, preferably from about 3% to about 10%, and more preferably from about 4% to about 8%.

PIGMENTS

A wide variety of pigments are contemplated for use with this invention. The pigment can be organic or inorganic. Preferably, the pigments are readily dispersable in an aqueous carrier.

Organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes.

Inorganic pigments include iron oxides, ultramarine and chromium or chromium hydroxide colors, and mixtures thereof.

Pigments may be coated or uncoated. A particularly preferred coating is magnesium myristate. Coatings can be hydrophilic or lipophilic, but are preferably hydrophilic.

The pigment is used in cosmetic composition of the present invention in an amount varying from about 2% by weight to about 35% by weight, preferably from about 5% to about 20%, and more preferably from about 7% to about 10%.

OPTIONAL INGREDIENTS

The composition and method of the present invention can utilize other compatible ingredients so long as they do not detract from the advantageous results of the present invention. Typically, such additional ingredients are included in an aggregate amount of less than about 20%, typically less than about 15%, and preferably less than about 10%. These include dyes, humectants, sunscreens, antioxidants, preservatives, fragrance, buffering agents and viscosity adjusters.

PREPARING PREFERRED COSMETIC VEHICLES

Generally, the first step in preparing preferred cosmetic compositions is to add the glycol to water. Then, the metal soap is added, which creates a rigid, brittle matrix. Then, the plasticizer is added, which softens and gives resilience to the matrix, forming the stick with a desirable resilient consistency. Next, cosmetically acceptable pigments are dispersed in the cosmetic composition.

To determine whether the cosmetic composition has the desired physical properties, a drop point analysis is used. This test is well known in the art, and it is very similar to a melting point test. A sample of the cosmetic composition is placed in a cup, which is then subjected to a beam of light. The temperature rises slowly and consistently. When a droplet falls, the temperature is recorded. Preferred drop point temperatures range from about 50 to about 70° C. more preferably from about 55 to about 65° C.

EXAMPLE

The following non-limiting example illustrates a cosmetic composition made in accordance with the present invention:

| INGREDIENTS | WEIGHT PERCENT |
| --- | --- |
| Jojoba Wax PEG-80 Esters | 9.0 |
| Butylene Glycol | 24.0 |
| Sodium Stearate | 4.5 |
| Iron Oxide Black & Sodium Stearoyl Glutamate & Trideceth-6 Carboxylate | 0.3 |
| Iron Oxide Red & Sodium Stearoyl Glutamate & Trideceth-6 Carboxylate | 0.4 |
| Iron Oxide Yellow & Sodium Stearoyl Glutamate & Trideceth-6 Carboxylate | 0.7 |
| $TiO_2$ & Sodium Stearoyl Glutamate & Trideceth-6 Carboxylate | 6.7 |
| DI Water | 47.9 |
| Optional Ingredients | 6.5 |

Of course, it should be understood that a wide range of changes and modifications can be made to the embodiments described above. It is intended, therefore, that the foregoing description illustrates rather than limits this invention, and that it is the following claims, including all equivalents that define this invention.

What is claimed is:

1. An oil-free cosmetic composition comprising:
    a) a plasticizer;
    b) a $C_{1-15}$ alkyl glycol;
    c) a metal soap;
    d) a pigment, the pigment being opaque and readily transferable to skin; and
    e) water, whereby the oil-free cosmetic composition has a consistency that is formable into a cosmetic stick.

2. The cosmetic composition of claim 1 wherein the plasticizer is a water-soluble natural wax.

3. The cosmetic composition of claim 1 wherein the plasticizer is a water-soluble synthetic wax.

4. The cosmetic composition of claim 1 wherein the plasticizer is selected from water-soluble polyethylene glycols and methoxy derivatives thereof, and mixtures thereof.

5. The cosmetic composition of claim 1 wherein the plasticizer is selected from the group consisting of water-soluble derivatives of jojoba wax, dimethicone copolyol, and mixtures thereof.

6. The cosmetic composition of claim 1 wherein the glycol is selected from the group consisting of propylene glycol, butylene glycol, hexylene glycol, and mixtures thereof.

7. The cosmetic composition of claim 1 wherein the metal soap is selected from the group consisting of sodium stearate and magnesium stearate.

8. The cosmetic composition of claim 1 wherein the pigment is coated.

9. The cosmetic composition of claim 1 wherein the pigment coating is hydrophilic.

10. The cosmetic composition of claim 1 in the form of a stick.

11. The cosmetic of claim 1 further comprising a sunscreen or a skin-whitener.

12. An oil-free cosmetic composition comprising:
    a) from about 0.5% to about 25% of a plasticizer;
    b) from about 1% to about 50% of a $C_{1-15}$ alkyl glycol;
    c) from about 2% to about 15% of a metal soap;
    d) from about 2% pigment to about 35% of a pigment, the pigment being opaque and readily transferable to skin; and
    e) from about 35% to about 70% of water, whereby the oil-free cosmetic composition has a consistency that is formable into a cosmetic stick.

13. The cosmetic composition of claim 12 wherein the plasticizer is a water-soluble natural wax.

14. The cosmetic composition of claim 12 wherein the plasticizer is a water-soluble synthetic wax.

15. The cosmetic composition of claim 12 wherein the plasticizer is selected from the group consisting of water-soluble derivatives of jojoba wax, dimethicone copolyol, and mixtures thereof.

16. The cosmetic composition of claim 12 wherein the metal soap is selected from the group consisting of sodium stearate, magnesium stearate, and mixtures thereof.

17. An oil-free cosmetic stick comprising:
    a) from about 0.5% to about 25% of a water-soluble wax;
    b) from about 1% to about 50% of a glycol selected from the group consisting of propylene glycol, diethylene glycol, ethylene glycol, butylene glycol, hexylene glycol, and mixtures thereof;

c) from about 2% to about 15% of a metal soap selected from the group consisting of sodium stearate, magnesium stearate, and mixtures thereof;

d) from about 2% to about 35% of pigment; and e) from about 35% to about 70% of water.

18. An oil-free cosmetic composition comprising:

a) a plasticizer;

b) a glycol;

c) a metal soap;

d) pigment; and e) water.

19. The composition of claim 18 wherein the composition is in the form of a stick and wherein the composition readily transfers opaque pigment to skin.

20. An oil-free cosmetic composition comprising:

a) from about 0.5% to about 25% of a plasticizer selected from the group consisting of water-soluble derivatives of jojoba wax, dimethicone copolyol, and mixtures thereof;

b) from about 1% to about 50% of a $C_{1-15}$ alkyl or alkenyl glycol;

c) from about 2% to about 15% of a metal soap selected from the group consisting of sodium stearate, magnesium stearate, and mixtures thereof;

d) from about 2% pigment to about 35% of a pigment, the pigment being opaque and readily transferable to skin; and e) from about 35% to about 70% of water such that the consistency of the cosmetic composition is formable into a stick.

21. An oil-free cosmetic composition comprising:

a) a plasticizer;

b) a glycol;

c) a metal soap;

d) pigment, the pigment being opaque and readily transferable to skin; and e) water, whereby the oil-free cosmetic composition has a consistency that is formable into a cosmetic stick.

* * * * *